(12) United States Patent
Lee et al.

(10) Patent No.: US 8,932,717 B2
(45) Date of Patent: *Jan. 13, 2015

(54) LIPOLYTIC ENZYME FOR FORMATION OF ANTI-FINGERPRINT COATING, METHOD OF FORMING ANTI-FINGERPRINT COATING, SUBSTRATE COMPRISING THE ANTI-FINGERPRINT COATING FORMED BY THE METHOD, AND PRODUCT COMPRISING THE SUBSTRATE

(75) Inventors: Eun Jeong Lee, Daejeon (KR); Young Jun Hong, Daejeon (KR); Hyeon Choi, Daejeon (KR); Taek Ho Yang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 154 days.

This patent is subject to a terminal disclaimer.

(21) Appl. No.: 13/496,855

(22) PCT Filed: Sep. 17, 2010

(86) PCT No.: PCT/KR2010/006442
§ 371 (c)(1),
(2), (4) Date: Mar. 16, 2012

(87) PCT Pub. No.: WO2011/034387
PCT Pub. Date: Mar. 24, 2011

(65) Prior Publication Data
US 2012/0177913 A1    Jul. 12, 2012

(30) Foreign Application Priority Data
Sep. 18, 2009    (KR) .................. 10-2009-0088587

(51) Int. Cl.
| C12N 9/20 | (2006.01) |
| C12N 9/96 | (2006.01) |
| C12N 11/14 | (2006.01) |
| C09D 5/16 | (2006.01) |
| C12N 11/08 | (2006.01) |

(52) U.S. Cl.
CPC .............. *C12N 11/14* (2013.01); *C09D 5/1687* (2013.01); *C12N 11/08* (2013.01)
USPC .......................... 428/411.1; 435/198; 435/188

(58) Field of Classification Search
CPC ........ C09D 5/00; C09D 5/006; C09D 5/1687; C09D 5/1693; C09D 7/12; C09D 7/125; C09D 7/1233; C09D 123/00; C09D 131/00; C12N 9/00; C12N 2310/00; C12N 2539/00; C12N 11/08; C12N 11/14; C12N 9/20; C08L 89/00; C08L 2205/00
See application file for complete search history.

(56) References Cited

U.S. PATENT DOCUMENTS

| 6,342,386 | B1 | 1/2002 | Powers et al. | |
| 2004/0247895 | A1 | 12/2004 | Dreja et al. | |
| 2005/0272141 | A1 | 12/2005 | Crawford | |
| 2008/0038241 | A1* | 2/2008 | Schasfoort et al. | .......... 424/94.3 |
| 2009/0238811 | A1* | 9/2009 | McDaniel et al. | ........... 424/94.2 |
| 2012/0219782 | A1* | 8/2012 | Lee et al. | ...................... 428/220 |

FOREIGN PATENT DOCUMENTS

| CA | 2402653 | | 3/2004 | |
| CN | 1440457 | | 9/2003 | |
| CN | 1522286 | A | 8/2004 | |
| DE | 19830848 | | 1/2000 | |
| EP | 1167521 | | 1/2002 | |
| EP | 1661955 | | 5/2006 | |
| JP | 63-168346 | A | 7/1988 | |
| JP | 63-171678 | | 7/1988 | |
| JP | 2533507 | B2 | 6/1996 | |
| JP | 2533507 | | 8/1996 | |
| JP | 09-118842 | A | 5/1997 | |
| JP | 3280024 | | 2/2002 | |
| JP | 2004-506089 | | 2/2004 | |
| JP | 2004-530027 | A | 9/2004 | |
| KR | 10-2001-0108263 | A | 12/2001 | |
| KR | 10-2003-0011802 | A | 2/2003 | |
| WO | 9313256 | | 7/1993 | |
| WO | 02/16521 | | 2/2002 | |
| WO | WO 2007051806 | A1 * | 5/2007 | ............... B05D 1/62 |
| WO | 2008063902 | | 5/2008 | |
| WO | 2008131715 | | 11/2008 | |
| WO | 2009-062518 | | 5/2009 | |
| WO | 2009062518 | | 5/2009 | |

OTHER PUBLICATIONS

English translation of WO 2007/051806A1.Vissing, K.-D. et al. 2007. Coating method and coated body.pp. 1-51; specif. pp. 5 and 33.*

* cited by examiner

*Primary Examiner* — John S Brusca
*Assistant Examiner* — Sharon M Papciak
(74) *Attorney, Agent, or Firm* — McKenna Long & Aldridge, LLP (57) ABSTRACT

Provided are a use of a lipolytic enzyme for forming anti-fingerprint coating, a method of forming anti-fingerprint coating including treating a substrate with a composition comprising the lipolytic enzyme, a substrate including the anti-fingerprint coating formed by the same method, and a product including the same. The anti-fingerprint coating can reduce contamination of display devices, appearances of electronic devices or building materials by fingerprints.

8 Claims, 10 Drawing Sheets

LIPOLYTIC ENZYME FOR FORMATION OF ANTI-FINGERPRINT COATING, METHOD OF FORMING ANTI-FINGERPRINT COATING, SUBSTRATE COMPRISING THE ANTI-FINGERPRINT COATING FORMED BY THE METHOD, AND PRODUCT COMPRISING THE SUBSTRATE

This application is a National Stage Entry of International Application No. PCT/KR2010/006442, filed Sep. 17, 2010, and claims the benefit of Korean Application No. 10-2009-0088587, filed on Sep. 18, 2009, which is hereby incorporated by reference for all purposes as if fully set forth herein.

TECHNICAL FIELD

The present invention relates to a novel use of a lipolytic enzyme for forming anti-fingerprint coating capable of providing a self cleaning function to a surface of a substrate, a method of forming anti-fingerprint coating using the lipolytic enzyme, a substrate including the anti-fingerprint coating formed by the same method, and a product including the same.

BACKGROUND ART

Contamination caused by fingerprints is one of the most frequent contaminations occurring on various display devices, high-glossy electronic devices or building materials. Such contamination is clearly visible and causes a defect in the appearance of a product. Recently, as the fingerprint contamination on a surface of a display device has increased with the development of touchscreen interface technology of electronic devices, there is an increasing demand for resolving the problem of the fingerprint contamination on the surface of display devices. However, until now, no technology of realizing anti-fingerprint coating has been actually developed, although anti-contamination coating has just been developed in the sense of easy cleaning.

For example, WO09/072738 discloses a anti-fingerprint coating composition for a stainless steel external case of an electronic appliance, which contains 27.6 to 36.2 parts by weight of polysilicate, 10.6 parts by weight or less of one resin selected from epoxy and vinyl resins, 21.2 to 42.6 parts by weight of colloidal silica, and 10.6 parts by weight or less of an additive composed of at least one selected from the first group consisting of —OH, —NH$_2$, and —COOH and at least one selected from the second group consisting of —CnF$_{2n+1}$, —SiR$_3$.

U.S. Patent No. 20020192181 discloses an anti-contamination composition, which includes a cured or crosslinked polymer having no perfluoropolyether moieties, and a fluid fluorinated alkyl- or alkoxy-containing polymer or oligomer.

However, the above-mentioned anti-contamination film uses fluorine-based coating, such that a contaminant transferred to its surface is easily wiped due to low surface energy. Since the anti-contamination film does not have a self-cleaning function, that is, a function of actively reducing transfer of fingerprints or decomposing fingerprints, the appearance may not be improved without wiping the contaminant off.

A conventional anti-fingerprint film can be applied only to a steel plate used for an external case, and has a limit in application to a product requiring high light transmittance such as a display device.

Meanwhile, a coating solution, a coating layer, and a coating method using the same were also developed in the self-cleaning sense using an enzyme. However, the coating solution, layer and method have been developed to prevent adherence of marine microorganisms to the bottom of a ship, but not to reduce contamination caused by fingerprints on display devices, the appearances of electronic devices, and building materials.

For example, a self-polishing, anti-contamination coating composition is disclosed in U.S. Patent No. 2008/0038241, and a method of preventing contamination of an underwater device by marine microorganisms is disclosed in U.S. Pat. No. 5,998,200.

That is, in the self-cleaning sense using an enzyme, the conventional coating solution, layer or method has a mechanism of previously removing an adsorbent material produced by marine microorganisms to prevent marine microorganisms from adhering to the bottom of a ship or removing a contaminant with the adsorbent material, but this mechanism is not associated with the decomposition of the fingerprint contaminant.

As far as the present inventors know, there is no technology of anti-fingerprint coating in the self-cleaning sense, which can be used to provide an anti-fingerprint property to the surface of a display device.

Technical Problem

The present invention is directed to a technique of removing, with no hiding or wiping of, fingerprints by decomposing components of a transferred fingerprint using an enzyme and reducing a deviation in a physical property between the fingerprint components.

The present invention is also directed to a method of forming anti-fingerprint coating which may reduce transfer of fingerprints and have a fingerprint decomposing property, a substrate including the anti-fingerprint coating prepared according to the same method, and a product including the same.

Technical Solution

The present inventors have made much research on a method of forming anti-fingerprint coating capable of providing a self-cleaning function, not simply forming an anti-contamination coating providing an easy cleaning function. In detail, in consideration that the fingerprint is mostly composed of lipids, the present inventors have assumed that when a lipolytic enzyme is coated on a substrate, transferred fingerprints may be reduced by the reaction of the enzyme. Accordingly, the present inventors have confirmed whether such coating provides an anti-fingerprint property by examining a change in a physical property of the fingerprint transferred to the lipolytic enzyme-coated substrate.

While major components of a fingerprint are sweat and sebum, the fingerprint is also composed of dead skin cells from the skin and contaminants such as dusts from an external environment. Among them, it has been known that the main cause leaving stains on an appearance of a product such as an electronic device is sebum, which is composed of lipids including triglycerides, wax monoesters, fatty acids, squalenes, cholesterols, cholesteryl esters, etc. (P. W. Wertz, Int. J Cosmet. Sci. 2009, 31: 21-25). Among the components of the sebum, the triglyceride and wax monoester account for nearly 70% of the total content of the sebum. These components have a structure in which several fatty acids are bound by ester bonds. When the ester bonds are broken down, the sebum is mainly decomposed into fatty acids, especially, oleic acids, leading to an increase in homogeneity and conversion into lower molecular weight materials. As a result, the sebum may be completely released from a product by decomposing the oleic acids into lower molecular weight materials or modifying the oleic acids to increase volatility.

Therefore, the present invention is directed to a novel use of a lipolytic enzyme for forming anti-fingerprint coating, that is, a method of forming anti-fingerprint coating using a lipolytic enzyme.

More particularly, the present invention is directed to a method of forming anti-fingerprint coating including treating the substrate with a composition comprising a lipolytic enzyme.

In the present invention, the lipolytic enzyme includes any enzymes having a characteristic of hydrolyzing lipid components of a fingerprint such as triglycerides, wax monoesters, fatty acids, squalenes, cholesterols and cholesteryl esters.

An example of an enzyme having an activity to hydrolyze ester bonds at room temperature is a lipase. The present invention is not limited to the kind or origin of the lipase, and thus any type of lipase may be used as the lipolytic enzyme according to one embodiment of the present invention. To obtain a high degree of hydrolysis with respect to the triglyceride and wax monoester, which are the main components of the sebum, a lipase non-specifically acting at any position may be used. Currently, various lipases produced using microorganisms may be commercially available from Novozymes or Amano Enzyme, and a lipase may be produced using a transformer into which a backbone gene of the lipase is inserted.

In addition to the lipase, the enzymes having a lipolytic activity are well known in the art. For example, a considerable number of proteases are known as lipolytic enzymes having lipolytic activity, and cutinases are also known to have lipolytic activity.

A composition comprising a lipolytic enzyme for forming anti-fingerprint coating may also include at least one enzyme selected from the group consisting of a protease, an amylase, a cellulase and a lactase. For example, to decompose various kinds of proteins smeared by a fingerprint, a protease may be immobilized on a surface of the product. The protease is used to break peptide bonds between proteins and thereby remove contamination. In addition, to remove components of sweat and components derived from various external contaminants, an enzyme such as an amylase, a cellulase or a lactase may be used.

In addition to the enzyme, the composition may further include a material capable of stabilizing the enzyme. For example, the composition may include a buffer such as a phosphate buffered saline (PBS), a potassium phosphate buffer, or a sodium phosphate buffer. To retain the activity of the enzyme, a polyhydric alcohol such as polyethyleneglycol or propylene glycol may be coated as the polymer on a substrate with the enzyme, or polyurethane, acryl-based organic material or a siloxane-based organic/inorganic compound may be coated on a substrate with the enzyme.

The composition other than the above-mentioned enzyme may be coated on the substrate with the enzyme at a time, or the enzyme and the composition may be sequentially coated on the substrate. That is, the composition excluding the enzyme may be coated on the substrate, and then the enzyme may be coated thereon by adsorption or covalent bonds.

Meanwhile, moisture is required for a lipolytic enzyme to hydrolyze lipids. Since the fingerprint includes moisture in addition to the lipid, there is no need to supply the moisture. However, to supply more moisture and improve stability of the enzyme, a hydrogel component may be included in the composition or coated on the surface of the substrate. To prepare the hydrogel component, a material having both a cross-linker containing at least two double bonds and a hydrophilic functional group may be used. Such a component may include ethylene glycols or acrylamides having a multifunctional group. Due to the supply of the moisture and the stability of the enzyme by hydrogel coating, the hydrolysis of the triglyceride and wax monoester may be further promoted.

Meanwhile, the present invention is not limited to the substrate having anti-fingerprint coating, and thus any type of substrate is applicable. For example, products requiring the anti-fingerprint coating are products that are often contacted with hands in everyday life, including display devices, appearances of electronic devices, and building materials. These products have a surface formed of plastic or glass, or a surface treated by gloss coating such as UV coating or protective coating. In one embodiment, the substrate may be formed of plastic or glass. For example, the substrate may include at least one polymer selected from polyester, polypropylene, polyethyleneterephthalate, polyethylenenaphthalate, polycarbonate, triacetylcellulose, olefin copolymer, and polymethylmethacrylate, or glass. The substrate may be treated on its surface by various coating methods such as gloss coating, protective coating, paint coating, and hydrogel coating.

The present invention is not particularly limited to a method of treating the substrate with the composition including a lipolytic enzyme, and thus any method known in the art will be used. A method of immobilizing an enzyme is known in the art. For example, a lipolytic enzyme may be introduced to the surface of the substrate by adsorption, covalent bonds or encapsulation.

The adsorption refers to adherence of the lipolytic enzyme to the surface of the substrate or a coating layer of an enzyme-free anti-fingerprint coating composition by physical cohesion. A protein constituting the enzyme has strong adsorption to a surface of a material alone. Thus, the lipolytic enzyme may be immobilized to the surface of the substrate by adsorption with no use of an additional treatment process. The following embodiment shows that the immobilization of the lipolytic enzyme by adsorption provides excellent stability.

To introduce the lipolytic enzyme to the surface of the substrate, there are various known techniques of forming covalent bonds between the substrate and the enzyme or between the coating layer of the enzyme-free anti-fingerprint coating composition and the enzyme. The techniques use a cyanogen bromide, an acid azide derivative, a condensing reagent, diazo coupling, alkylation, and carrier crosslinking.

For example, the carrier crosslinking technique is a technique of forming covalent bonds between a functional group present on the surface of the substrate and a functional group present on the surface of the substrate and a functional group present on the lipolytic enzyme using a bifunctional crosslinker. Since the lipolytic enzyme has various functional groups in addition to an amino group and a carboxyl group, if a functional group capable of covalently binding to these functional groups is present in the surface of the substrate, the covalent bonds may be easily formed using the bifunctional crosslinker. Here, the functional group present on the surface of the substrate may be a functional group originally present on the substrate or a functional group introduced to the surface of the substrate to form the covalent bonds or included in the enzyme-free anti-fingerprint coating composition. For example, when the substrate is formed of plastic, the functional group present on the surface of the substrate may be directly used, and a desired functional group may be introduced to the surface by plasma or primer treatment. When the substrate is formed of glass, the functional group may be introduced to the surface by self-assembled monolayer (SAM) treatment using a siloxane-based organic compound, but the present invention is not limited thereto. As a functional group for forming covalent bonds with the enzyme, an amino group, an amide group, a carboxyl group, an aldehyde group, a hydroxyl group, or a thiol group is used, and the functional group present on or introduced to the surface of the substrate may vary according to the kind of the substrate.

In one embodiment, the covalent bond may be formed by a process including a) treating a substrate having at least one functional group selected from the group consisting of amino, amide, carboxyl, aldehyde, hydroxyl and thiol groups with a solution including a bifunctional crosslinker; and b) dipping the substrate in a buffer including the lipolytic enzyme.

As a bifunctional crosslinker used to induce formation of the covalent bonds, a bis-imidoester, bis-succinimidyl derivative, bifunctional aryl halide, bifunctional acrylating agent, dialdehyde, or diketone may be used, but the present invention is not limited thereto. An exemplary embodiment of the present invention shows the covalent bond being induced using dialdehyde, for example, glutaraldehyde.

In another embodiment, the covalent bond may be formed by dipping the substrate having an epoxy group at a surface thereof in the buffer including the lipolytic enzyme. Furthermore, as the substrate undergoing the above process is treated with heat or UV at a level in which the heat or UV does not degrade the activity of the enzyme, the enzyme may be more strongly immobilized.

A method of immobilizing the enzyme using the covalent bond as described above will be described in further detail with reference to the following exemplary embodiments.

In addition, the encapsulation refers to a method of immobilizing the enzyme by trapping the lipolytic enzyme between other materials. In an embodiment, the encapsulation may be performed by coating the surface of the substrate with a gel matrix, microcapsule, hollow fiber or membrane, and introducing the lipolytic enzyme. For example, a membrane formed of cellulose such as cellulose nitrate or cellulose acetate, polycarbonate, nylon, or fluororesin such as polytetrafluoroethylene may be used.

The coating of the substrate with a gel matrix, microcapsule, hollow fiber or membrane and the introduction of the lipolytic enzyme may be simultaneously or sequentially performed. In other words, the surface of the substrate is first coated with the gel matrix, microcapsule, hollow fiber or membrane, and the substrate is then dipped in the buffer including the lipolytic enzyme. Otherwise, the lipolytic enzyme may be introduced as soon as the surface of the substrate is coated with the gel matrix, microcapsule, hollow fiber or membrane. For example, for the encapsulation technique using the gel matrix, the gel matrix may be coated and cured, and the enzyme may then be adsorbed, or when a sol solution is prepared in a sol-gel reaction, the enzyme may be added to prepare a mixed solution and the substrate may be coated with the mixed solution and then cured.

Among the methods, the encapsulation using the gel matrix is more desirable to retain and further promote the activity of the enzyme. Any kind of gels ensuring a mechanical strength and an optical property may be applied. For example, the substrate may be primarily coated with a coating layer prepared by a sol-gel method using tetramethoxysilane (TMOS), tetraethoxysilane (TEOS) or glycidoxypropyl trimethoxysilane (GPTMS) or a hydrogel forming a double network by reinforcing a mechanical strength of polyethylene glycol, and the enzyme is then encapsulated into the primary coating. Further detailed description will be provided in the following exemplary embodiment.

As the buffer including the lipolytic enzyme used in the above-described methods, a PBS buffer, potassium phosphate buffer, or sodium phosphate buffer may be used, and the present invention is not limited thereto. An amount of the lipolytic enzyme included in the buffer is determined in principle as an amount at which the surface of the substrate to be immobilized may be covered with a monolayer. A generally used lipolytic enzyme is composed of a small amount of enzyme and additives including an excess of an extender such as dextrin or lactose and a stabilizer. Thus, the amount of the enzyme to be added is determined based only on the content of the protein. In the case of the covalent bond, the amount of the enzyme to be added may be determined by calculating a content of the protein corresponding to the functional group of the surface of the substrate, and in the cases of the adsorption and encapsulation, an amount of the enzyme to be added, which is 3 to 10 times the content of the protein capable of covering the surface of the substrate, may be dissolved in the buffer.

The present invention is also directed to a substrate including the anti-fingerprint coating formed by the above-described method. As seen from the following exemplary embodiments, the substrate including the anti-fingerprint coating to which a lipolytic enzyme is immobilized according to the method exhibits an anti-fingerprint characteristic because of decomposition of fingerprints and a decrease in transfer of fingerprints. Such anti-fingerprint coating may be stacked on the surface of the substrate in a single layer or multiple layers. The anti-fingerprint coating may be formed on the surface of the substrate to have a thickness of 20 nm to 200 μm. A single layer of coating may be formed with a thickness of 20 nm, and the coating may be carried out up to a thickness of 200 μm according to the kind and content of the coating composition. However, the thickness of the coating needs to be adjusted to a thickness level in which the optical property required for the substrate is not degraded. When the thickness of the anti-fingerprint coating layer is less than 20 nm, the decomposition of the fingerprint components may be limited, and when the thickness of the anti-fingerprint coating layer is more than 200 μm, the optical transmittance may be degraded.

To maximize a spreading effect of the fingerprint components, the anti-fingerprint coating layer may have a surface energy of 20 to 50 mN/m. When the surface energy of the anti-fingerprint coating layer is less than 20 mN/m, the fingerprint components may not spread, and when the surface energy of the anti-fingerprint coating layer is more than 50 mN/m, the fingerprint may be difficult to easily remove. Here, when a lipase is, for example, coated as the enzyme, the coating layer has a surface energy of 30 to 50 mN/m in which the spreading effect of the fingerprint is maximized As a result, since the transfer of the fingerprints is reduced, the range of the surface energy may be preferred.

The present invention is also directed to a product including the substrate including the anti-fingerprint coating. The product including the substrate including the anti-fingerprint coating according to the present invention may be a product that is often contacted with hands in everyday life, and the present invention is not particularly limited to the kind of the product. For example, the product may include display devices, electronic devices, or building materials. The display device may be one selected from the group consisting of a liquid crystal display device (LCD), an organic light emitting diode (OLED), and a plasma display device panel (PDP). Since currently-supplied portable display devices have a touchscreen-type interface, the introduction of the anti-fingerprint coating according to one embodiment of the present invention may cause the significant improvement of beauty of the product.

The present invention is not particularly limited to a method of introducing the anti-fingerprint coating to the product. In other words, the lipolytic enzyme may be directly coated on a substrate surface of the product such as the display device, or the film-type substrate coated with the lipolytic enzyme may be adhered to the surface of the product.

BRIEF DESCRIPTION OF THE DRAWINGS

The above and other objects, features and advantages of the present invention will become more apparent to those of ordinary skill in the art by describing in detail exemplary embodiments thereof with reference to the adhered drawings, in which.

DETAILED DESCRIPTION OF EXEMPLARY EMBODIMENTS

Hereinafter, the present invention will be described with reference to examples and comparative examples in detail. However, the present invention is not limited to these examples.

EXAMPLES

Example 1

Immobilization of Lipolytic Enzyme Using Covalent Bonds

A lipase was coated on a glass substrate by the following method.

A slide glass whose surface was coated with amino alkyl silane was reacted in 10% glutaraldehyde solution for 2 hours. Subsequently, the slide glass was lightly washed with distilled water, dipped in a PBS buffer having 100 mg/ml of a lipase (Amano Enzyme; Lipase PS "Amano" SD; derived from *Burkholderia cepacia*), and then kept at a room temperature for 24 hours. The lipase-immobilized slide glass was sufficiently washed with running distilled water, and washed in distilled water for 40 minutes with gentle shaking. Then, the slide glass was taken out, and blow-dried with compressed nitrogen at a room temperature. Thus, the preparation of a lipase-coated glass substrate was completed.

Experimental Example 1

Figure 1:
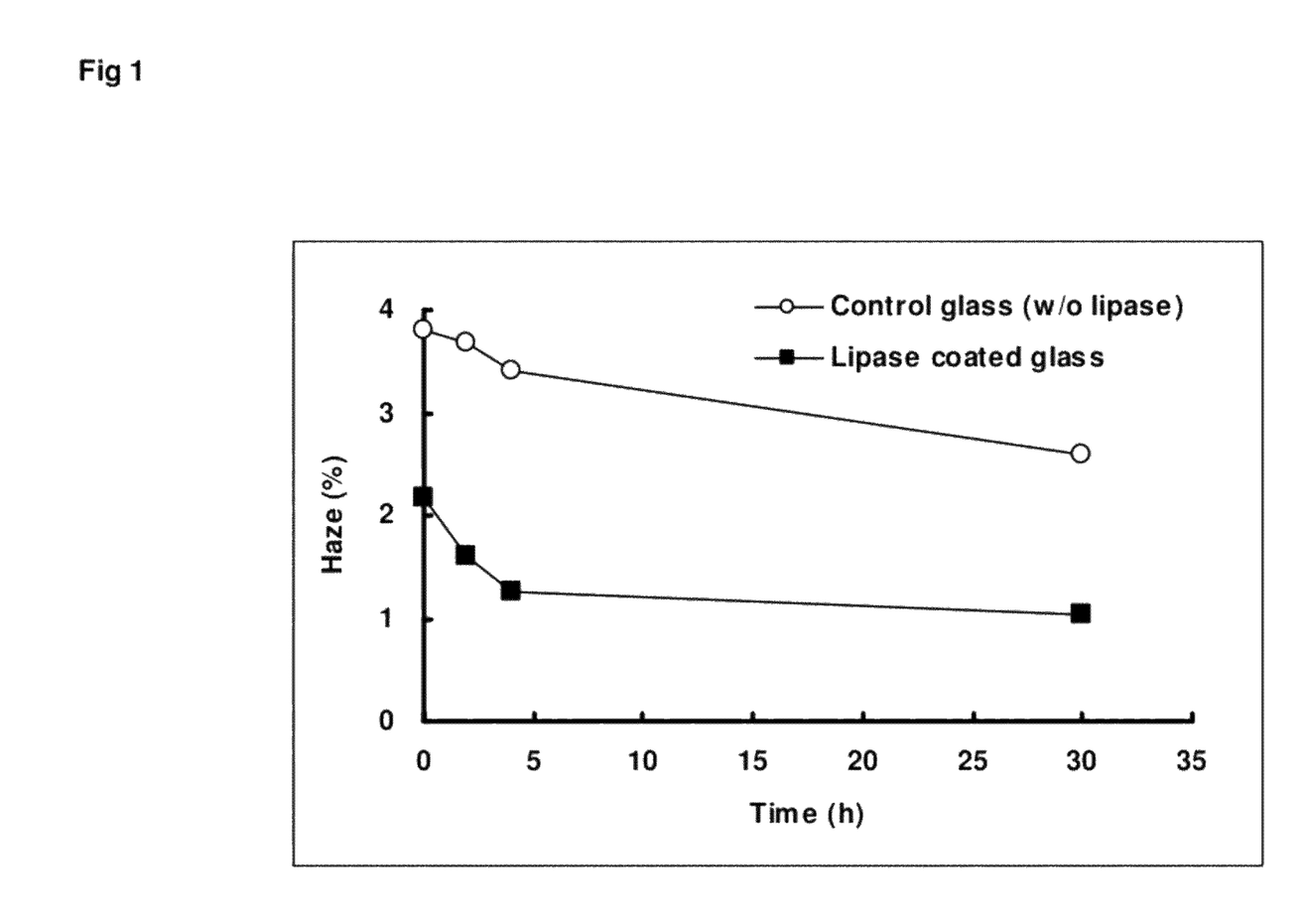
FIG. 1 is a graph of haze values measured after fingerprints are transferred to a substrate including an anti-fingerprint coating formed in Example 1.

Examination of Decrease in Degree of Transfer of Fingerprints by Anti-Fingerprint Coating Three samples were prepared by transferring fingerprints to the lipase-immobilized slide glasses as shown in Example 1, and measured for haze values according to time. The results are shown in FIG. 1. Here, as a control glass (without a lipase), a slide glass treated with amino alkyl silane and glutaraldehyde was prepared for comparison.

When the haze values were measured immediately after the fingerprints were left (0 hr), it was seen that the lipase-coated substrate shows a lower haze value than the control glass, which indicates that the fingerprints was less smeared on the lipase-coated substrate. Also, it was seen that the haze value is decreased as the fingerprint on the lipase-coated substrate was decomposed with time.

As described above, by an experiment of transferring the fingerprint to the lipase-immobilized surface, examining the resulting surface using a microscope, and measuring a haze value, it was seen that the lipase-immobilized surface had a lower degree of transfer of fingerprint than the surface without the lipase.

Example 2

Immobilization of Lipolytic Enzyme Using Epoxy Group

An immobilizing method using an epoxy group was performed, instead of the method of coating a lipase using chemical covalent bonds described in Example 1. The epoxy group-treated slide glass (superchip glass ES; slide epoxy silane; Nunc™) was dipped in a sodium phosphate buffer having 100 mg/ml of a lipase, and kept at a room temperature for 4 hours. Afterwards, the slide glass was reacted in an oven at 50 to 55° C. for 30 minutes. The slide glass was rinsed 15 to 20 times in distilled water, and washed with a sufficient amount of distilled water three times for 20 minutes. The slide glass was blow-dried with compressed nitrogen at a room temperature.

Example 3

Immobilization of Hydrolase to Gel Matrix by Adsorption

A surface of a substrate was coated with a hydrolase by adsorption using a gel matrix. According to this method, the gel matrix stabilized the enzyme, such that the efficiency of the enzyme was increased, and functional coating could be simultaneously performed using various gel matrixes. A lipase may be used as the enzyme alone, or in a combination of lipase and amylase or lipase and protease. First, the gel matrix was coated on a slide glass using a siloxane-based composition, which was performed according to Example 1 disclosed in Korean Patent Publication No. 1998-0002185. The gel matrix slide prepared thus was dipped in PBS buffer having 100 mg/ml of an enzyme, and kept at a room temperature for 24 hours. The slide was taken out, washed in the same manner as in Example 2, and blow-dried with compressed nitrogen at room temperature.

Experimental Example 2

Confirmation of Lipolytic Effect by Anti-Fingerprint Coating

Figure 2:
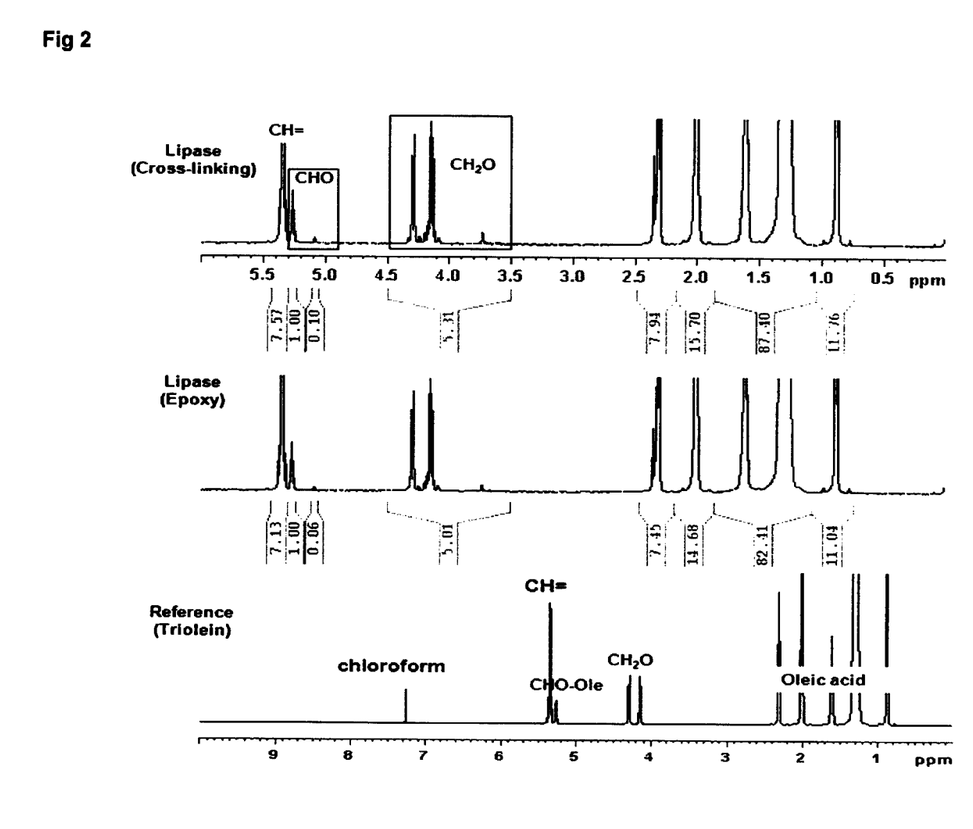
FIGS. 2 and 3 are NMR spectrums for decomposition results obtained after major fingerprint components are transferred to substrates including anti-fingerprint coatings formed in Examples 1 and 2.
Figure 3:
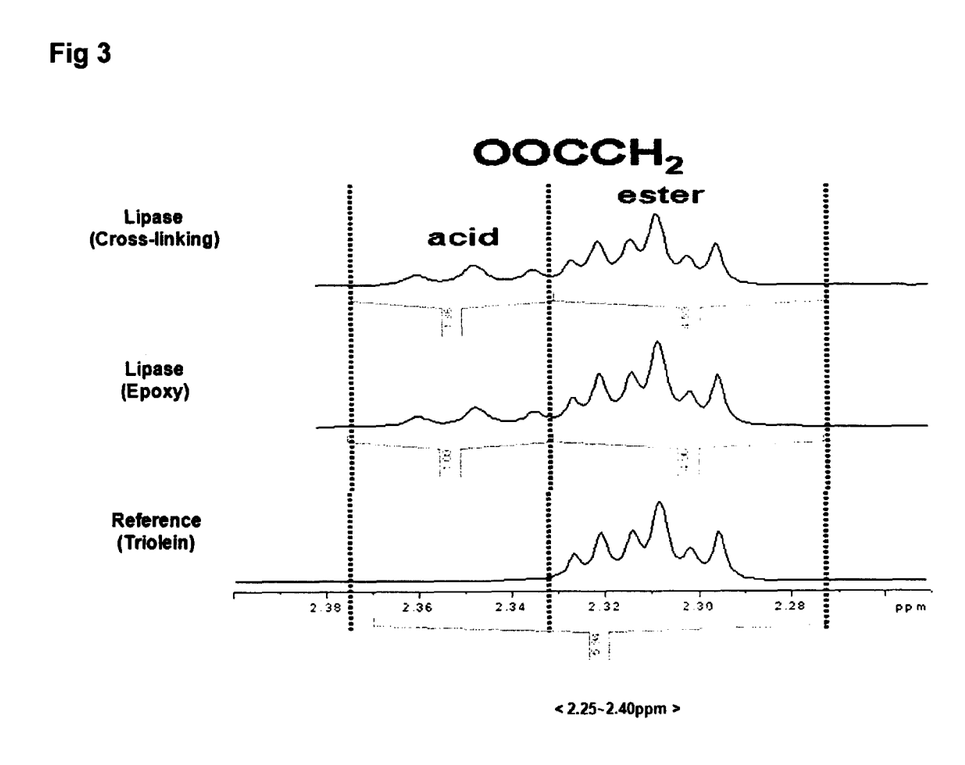

To confirm fingerprint decomposing performance from a glass prepared by coating a lipase by the same chemical covalent bond method as described in Examples 1 and 2, this experiment was performed using the main component, triglyceride, of a fingerprint. The triglyceride was a triolein, which was coated on a surface of the glass and kept at a room temperature for 24 hours. Afterwards, $^1$H-NMR analysis was performed to examine whether the triolein was decomposed or not. As a result, as shown in FIGS. 2 and 3, it was seen that an acid peak which did not appear from the reference (triolein) was observed from the lipase-coated slide.

Experimental Example 3

Confirmation of Lipolytic Effect by Anti-Fingerprint Coating

Figure 4:
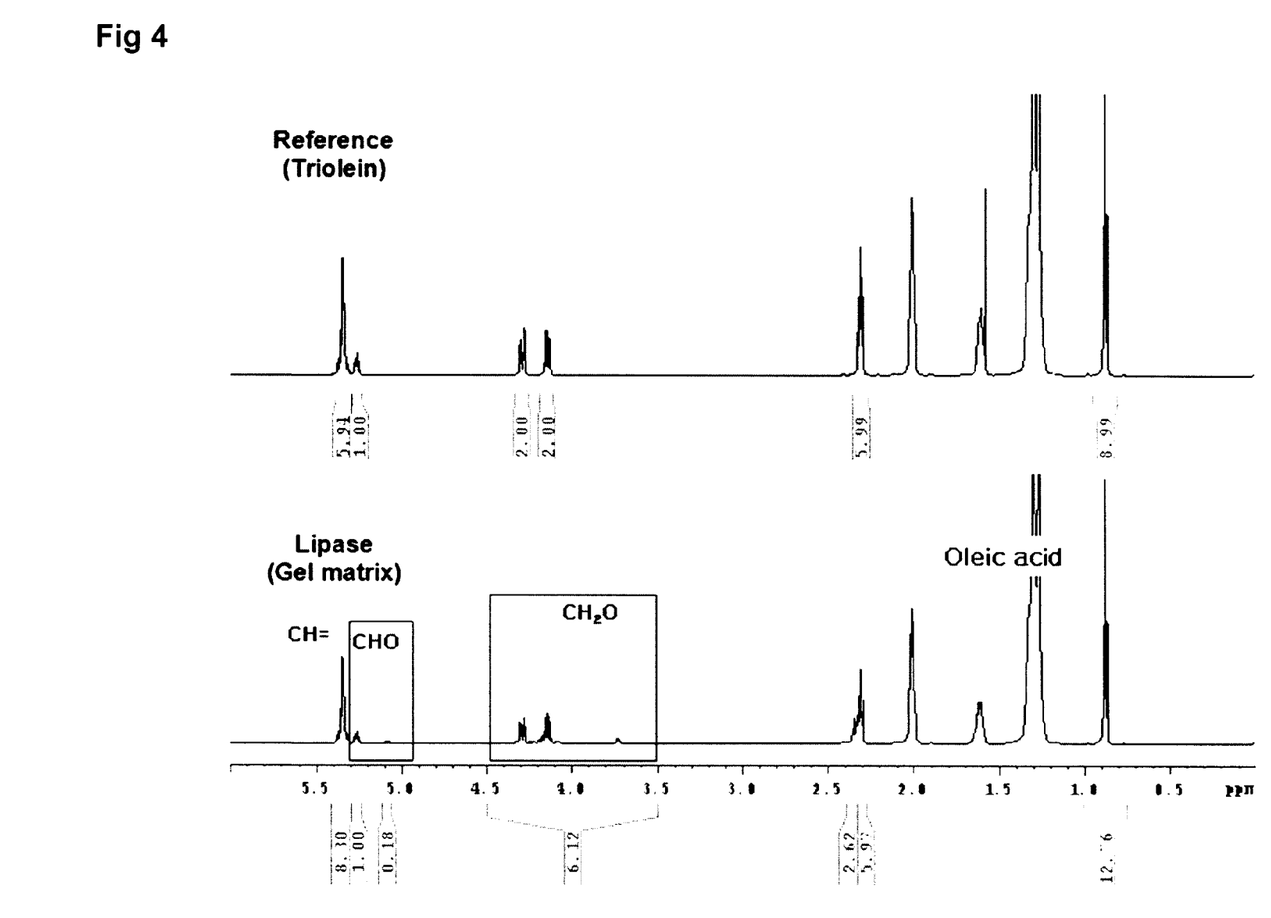
FIGS. 4 and 5 are NMR spectrums for decomposition results obtained after major fingerprint components are transferred to a substrate including anti-fingerprint coating Example 3.
Figure 5:
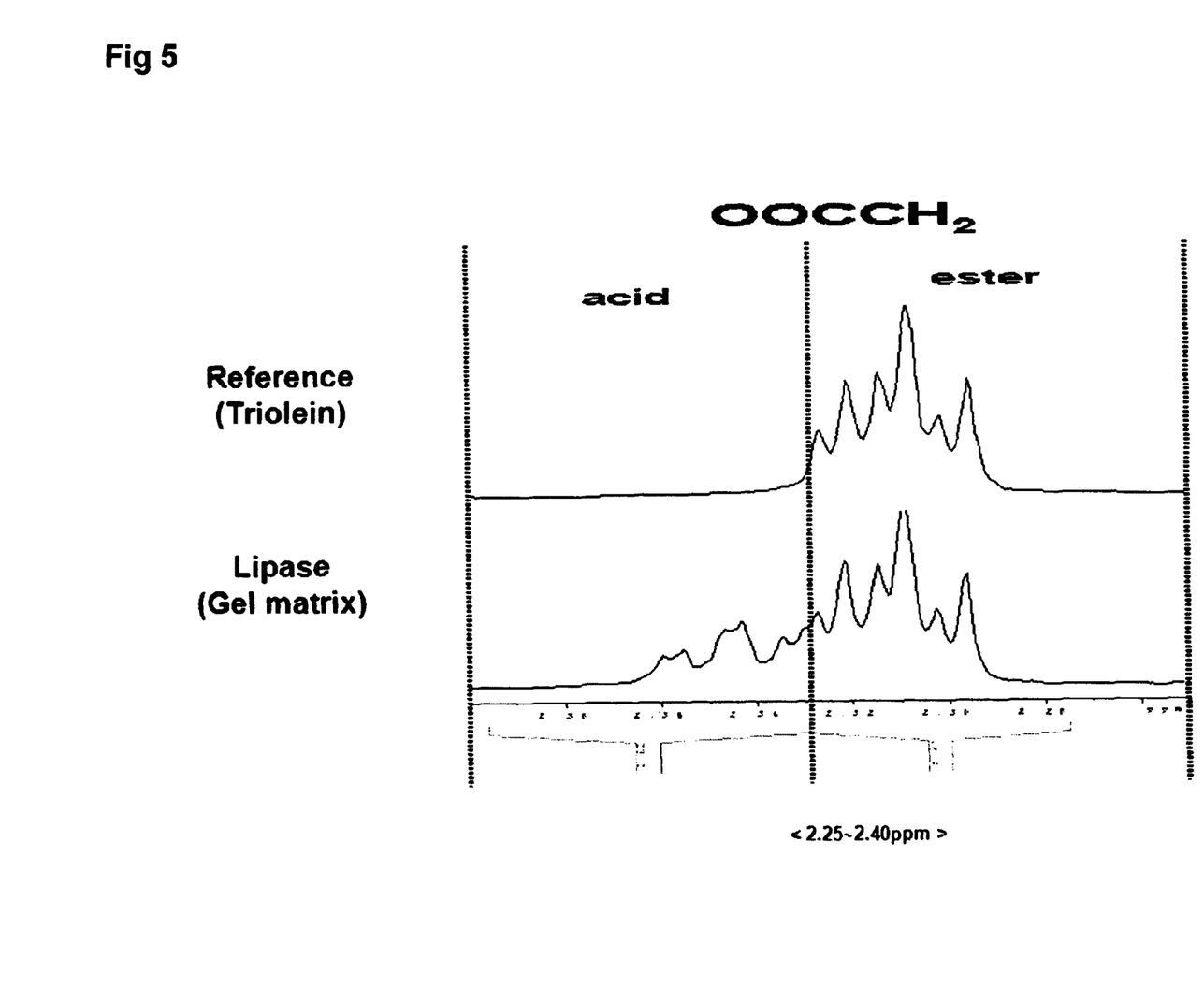

To confirm fingerprint decomposing performance from a glass prepared by coating a lipase with a gel matrix as described in Example 3, an experiment was performed using the main component of a fingerprint, a triglyceride. Afterwards, $^1$H-NMR analysis was performed to examine whether the triolein was decomposed or not. As a result, as shown in FIGS. 4 and 5, it was seen that an acid peak which was not seen from the reference (triolein) was shown from the lipase-coated slide.

Experimental Example 4

Figure 6:
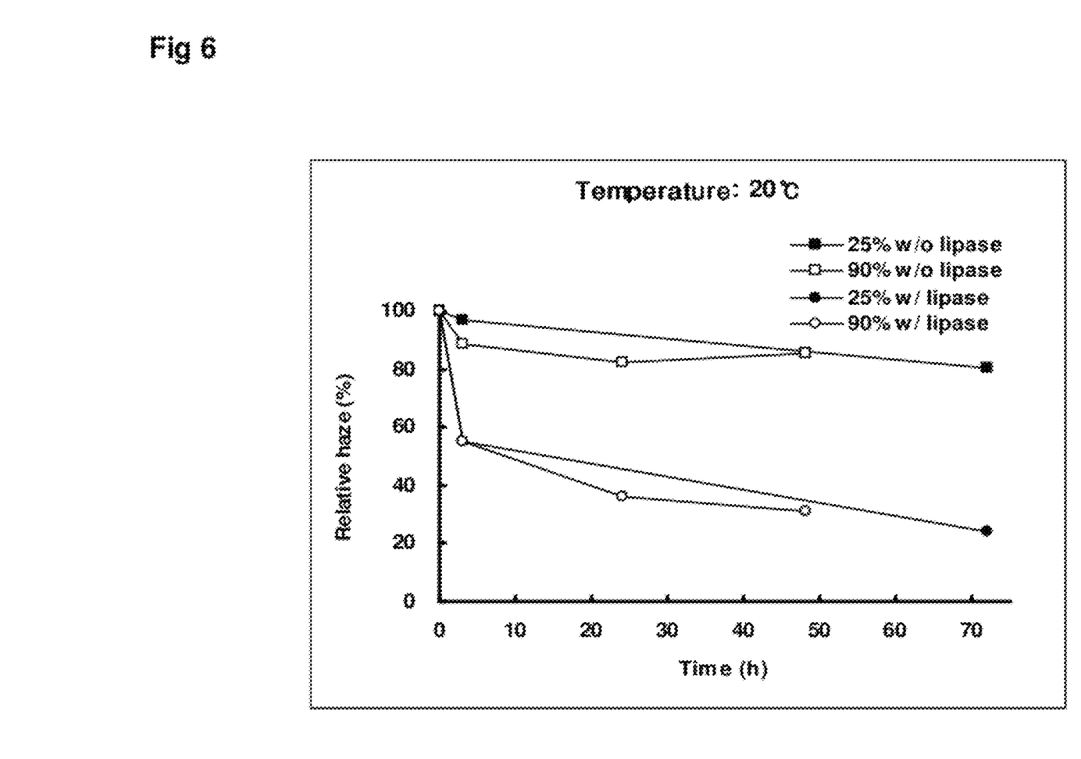
FIGS. 6 and 7 are graphs showing disappearance of fingerprints measured using a hazemeter after real fingerprints are transferred to the substrate including the anti-fingerprint coating formed in Example 3.
Figure 7:
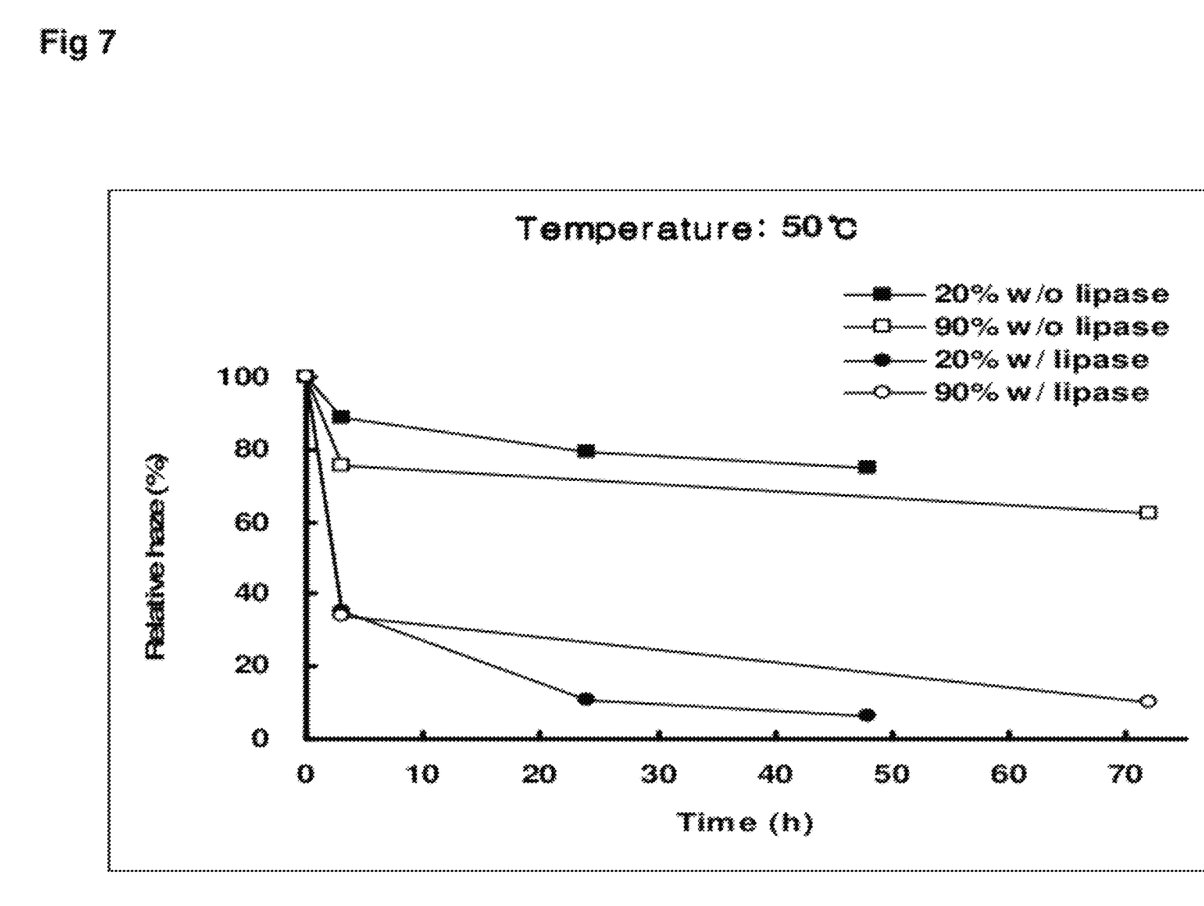

Confirmation of Fingerprint Decomposition Performance by Anti-Fingerprint Coating To confirm fingerprint decomposing performance from a glass prepared by coating a lipase together with a gel matrix in the same manner as described in Example 3, haze values were measured to examine a degree of disappearance of a fingerprint really transferred from a palm. The change in haze with time was observed for 48 to 96 hours under various temperature and humidity conditions using a temperature and humidity tester. The results are shown in FIGS. 6 and 7. The change in haze value (ΔH) with time was exhibited, provided that the haze value (ΔH) increased by fingerprint transfer was set to 100%. Compared to a lipase-free sample (shown as "w/o lipase") prepared in the same manner as described in Example 3, a significant decrease in haze was seen from the lipase-treated sample (shown as "w/lipase").

Experimental Example 5

Confirmation of Fingerprint Decomposing Performance by Anti-Fingerprint Coating

A wiping test was performed to confirm that immobilization of a lipolytic enzyme by adsorption was very stable on a glass prepared by coating with a lipase together with a gel matrix according to the method described in Example 3.

Figure 8:
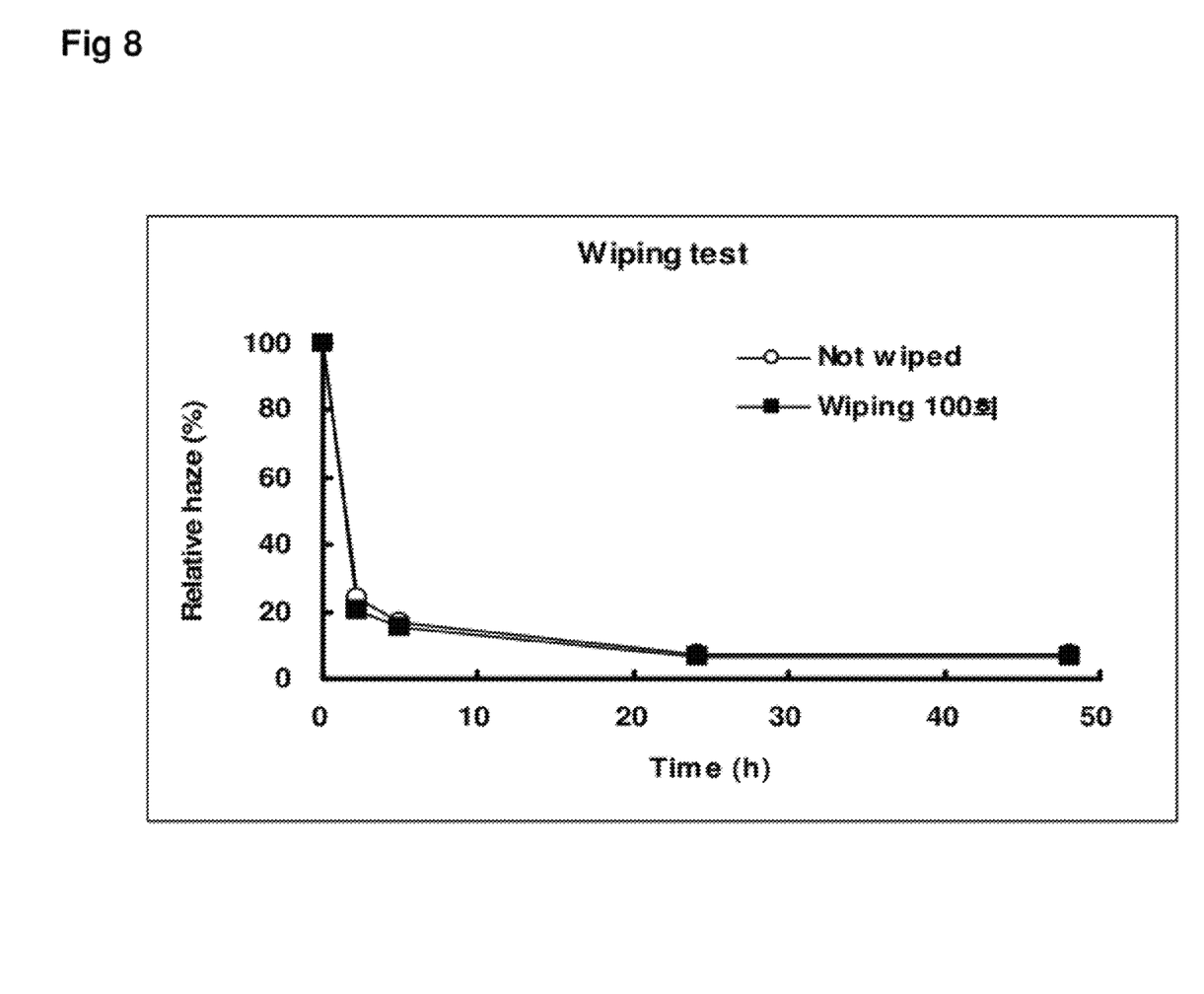
FIG. 8 is a graph showing disappearance of fingerprints measured using a hazemeter after the real fingerprints are transferred when a wiping test is performed on the substrate including the anti-fingerprint coating formed in Example 3.

A wiped sample was prepared by pressing a glass sample with a weight of 1 kg and wiping the glass sample 100 times with a dust-free fabric. Transfer of a real fingerprint was performed on the sample and a non-wiped sample, and then a degree of disappearance of the fingerprint was examined by measuring a haze value. The change in haze with time was observed for 48 hours under conditions including a temperature of 50° C. and a relative humidity of 30% using the temperature and humidity tester. The results are shown in FIG. 8. The change in ΔH with time was exhibited, provided that the haze value (ΔH) increased by fingerprint transfer was set to 100%. Compared to the sample (shown as "not wiped") which was prepared in the same manner as in Example 3 but not wiped, it was confirmed that no decrease in performance was observed from the wiped sample (shown as "wiped 100 times").

Experimental Example 6

Confirmation of Fingerprint Decomposing Performance by Anti-Fingerprint Coating

Figure 9:
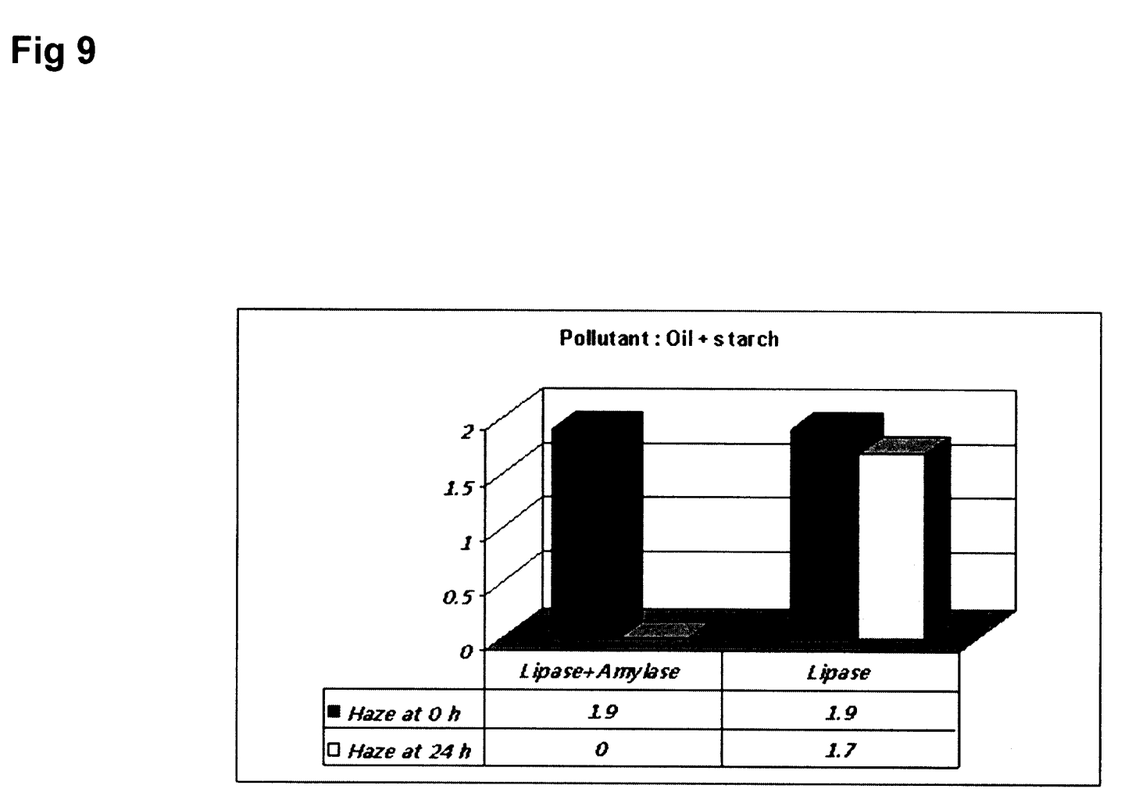
FIGS. 9 and 10 are graphs showing disappearance of a contaminant measured using a hazemeter when mixed contaminants are applied to the substrate including the anti-fingerprint coating formed in Example 3.
Figure 10:
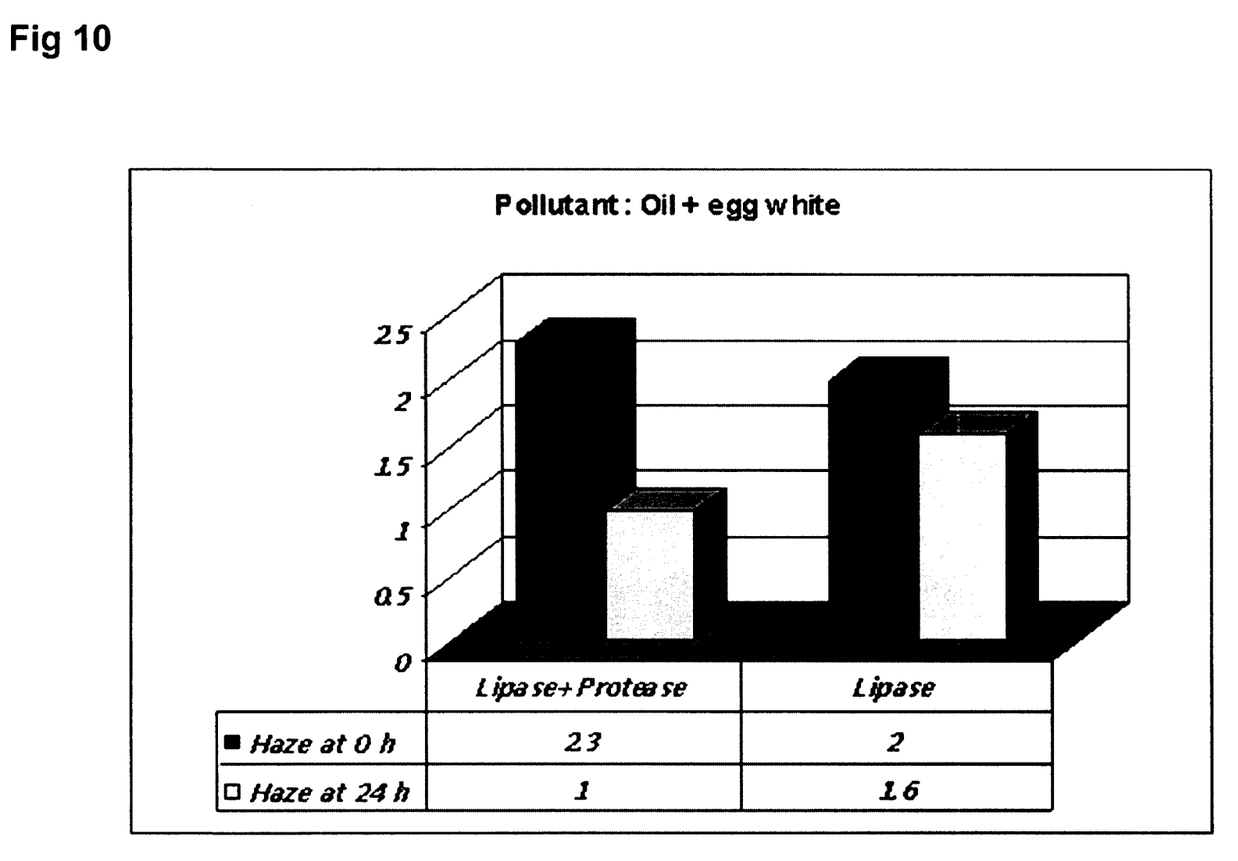

Experiments were performed to examine which of glasses prepared by coating with the enzyme together with a gel matrix in the same manner as described in Example 3 or by adding a different hydrolase other than the lipase exhibits more excellent performance to decompose various contaminants Three kinds of samples, including a sample prepared by adding a lipase alone, a sample prepared by adding an amylase with a lipase, and a sample prepared by adding a protease with a lipase, were prepared to confirm a degree of removal of each contaminant by measuring a haze value. A contaminant prepared by mixing oil and starch was transferred, and then the change in haze with time was observed. The results are shown in FIG. 9. A contaminant prepared by mixing oil and the white of an egg was transferred, and the change in haze with time was observed. The results are shown in FIG. 10. According to the two experiments, it was confirmed that the performance of removing the mixed contaminants was improved when another hydrolase was added with the lipase, compared to when the lipase alone was added.

From the result, it was seen that the present invention can realize anti-fingerprint performance by coating an enzyme on a surface of the substrate by a relatively simple method, and thus can be applied to almost all substrates requiring the anti-fingerprint characteristic.

Contamination of display devices, appearances of the electronic devices and building materials by fingerprints can be reduced using anti-fingerprint coating according to the present invention.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method of forming anti-fingerprint coating, comprising:
   providing a substrate which is selected from plastic or glass, and
   treating the substrate with a composition comprising a lipolytic enzyme to obtain an anti-fingerprint coating.

2. The method according to claim 1, wherein the lipolytic enzyme is a lipase.

3. The method according to claim 2, wherein the composition further includes at least one enzyme selected from the group consisting of a protease, an amylase, a cellulase, and a lactase.

4. The method according to claim 1, wherein the plastic includes at least one polymer selected from the group consisting of polyester, polypropylene, polyethyleneterephthalate, polyethylenenaphthalate, polycarbonate, triacetylcellulose, olefin copolymers, and polymethylmethacrylate.

5. The method according to claim 1, wherein the lipolytic enzyme is introduced to a surface of the substrate by adsorption, covalent bonds, or encapsulation.

6. The method according to claim 5, wherein the covalent bond is formed through a process including treating the surface of the substrate having at least one functional group selected from the group consisting of amino, amide, carboxyl, aldehyde, hydroxyl and thiol groups with a solution including a bifunctional cross-linker; and dipping the substrate in a buffer including the lipolytic enzyme.

7. The method according to claim 5, wherein the covalent bond is formed through a process including dipping the substrate having an epoxy group at a surface thereof in a buffer including the enzyme.

8. The method according to claim 5, wherein the encapsulation is performed by coating the surface of the substrate with a gel matrix, a microcapsule, a hollow fiber or a membrane, and introducing the lipolytic enzyme.

* * * * *

(12) INTER PARTES REVIEW CERTIFICATE (2186th)
United States Patent (10) Number: US 8,932,717 K1
Lee et al. (45) Certificate Issued: Jul. 7, 2021

(54) LIPOLYTIC ENZYME FOR FORMATION OF ANTI-FINGERPRINT COATING, METHOD OF FORMING ANTI-FINGERPRINT COATING, SUBSTRATE COMPRISING THE ANTI-FINGERPRINT COATING FORMED BY THE METHOD, AND PRODUCT COMPRISING THE SUBSTRATE

(75) Inventors: Eun Jeong Lee; Young Jun Hong; Hyeon Choi; Taek Ho Yang (73) Assignee: LG CHEM, LTD.

Trial Number:

IPR2018-01520 filed Aug. 6, 2018

Inter Partes Review Certificate for:

Patent No.: 8,932,717
Issued: Jan. 13, 2015
Appl. No.: 13/496,855
Filed: Mar. 16, 2012

The results of IPR2018-01520 are reflected in this inter partes review certificate under 35 U.S.C. 318(b).

INTER PARTES REVIEW CERTIFICATE
U.S. Patent 8,932,717 K1
Trial No. IPR2018-01520
Certificate Issued Jul. 7, 2021

AS A RESULT OF THE INTER PARTES REVIEW PROCEEDING, IT HAS BEEN DETERMINED THAT:

Claims 1-8 are cancelled.

9. (substitute for claim 1) *A method of forming an anti-fingerprint coating for a display device, comprising: providing a substrate which is selected from plastic or glass, wherein the substrate is a surface of the display device or is a substrate capable of being adhered to the surface of the display device; and*
*treating the substrate with a composition comprising a lipolytic enzyme to obtain an anti-fingerprint coating that reduces the transfer of a fingerprint and decomposes the fingerprint;*
*wherein the anti-fingerprint coating decreases the visibility of the fingerprint on a display device without wiping off the fingerprint;*
*wherein the visibility of the fingerprint on the display device is decreased when (i) a first haze value attributable to a fingerprint transferred to the substrate with the anti-fingerprint coating is lower than a second haze value attributable to a fingerprint transferred to a substrate without the anti-fingerprint coating, and (ii) the first and second haze values are measured at the same predetermined time point following fingerprint transfer.*

10. (substitute for claim 2) *The method according to claim 9, wherein the lipolytic enzyme is a lipase, the predetermined time point is within four hours following fingerprint transfer, and the first haze value at the predetermined time point is approximately 42-63% lower than the second haze value.*

11. (substitute for claim 3) *The method according to claim 10, wherein the composition further includes at least one enzyme selected from the group consisting of a protease, an amylase, a cellulose, and a lactase.*

12. (substitute for claim 4) *The method according to claim 9, wherein the plastic includes at least one polymer selected from the group consisting of polyester, polypropylene, polyethyleneterephthalate, polyethylenenaphthalate, polycarbonate, triacetylcellulose, olefin copolymers, and polymethylmethacrylate.*

13. (substitute for claim 5) *The method according to claim 9, wherein the lipolytic enzyme is introduced to a surface of the substrate by adsorption, covalent bonds, or encapsulation.*

14. (substitute for claim 6) *The method according to claim 13, wherein the covalent bond is formed through a process including treating the surface of the substrate having at least one functional group selected from the group consisting of amino, amide, carboxyl, aldehyde, hydroxyl and thiol groups with a solution including a bifunctional cross-linker; and dipping the substrate in a buffer including the lipolytic enzyme.*

15. (substitute for claim 7) *The method according to claim 13, wherein the covalent bond is formed through a process including dipping the substrate having an epoxy group at a surface thereof in a buffer including the enzyme.*

16. (substitute for claim 8) *The method according to claim 13, wherein the encapsulation is performed by coating the surface of the substrate with a gel matrix, a microcapsule, a hollow fiber or a membrane, and introducing the lipolytic enzyme.*

\* \* \* \* \*